Jan. 8, 1974 A. W. FISCHER Plant Pat. 3,427
AFRICAN VIOLET PLANT
Filed Jan. 24, 1972
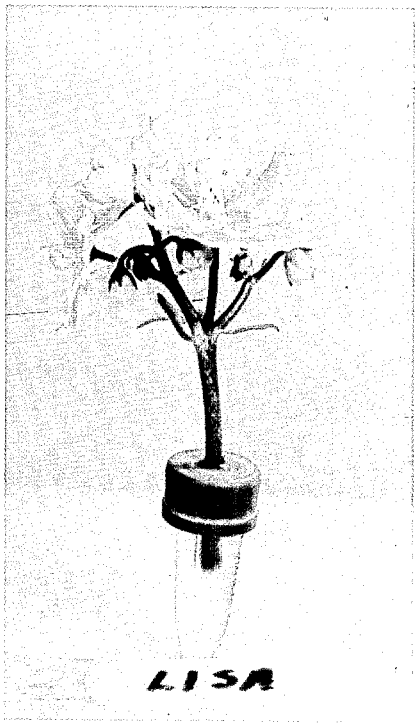
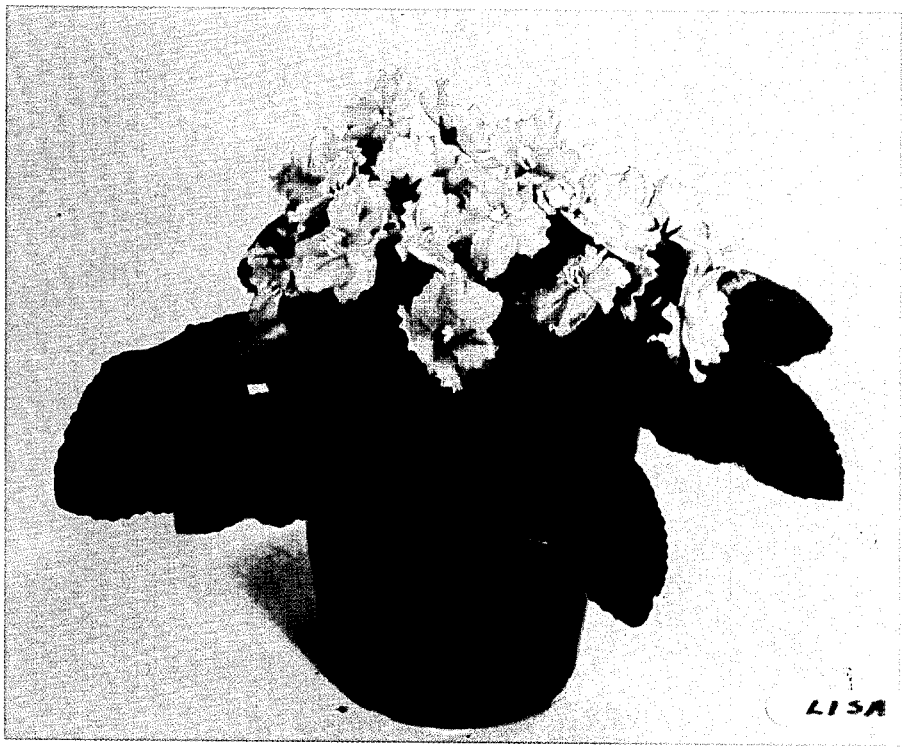

United States Patent Office

Plant Pat. 3,427
Patented Jan. 8, 1974

3,427
AFRICAN VIOLET PLANT

Arnold W. Fischer, Isernhagen, Germany, assignor to Geo. J. Ball, West Chicago, Ill.

Filed Jan. 24, 1972, Ser. No. 220,505
Int. Cl. A01h 5/00
U.S. Cl. Plt.—69 1 Claim

ABSTRACT OF THE DISCLOSURE

A new variety of African violet plant distinguished by its very profuse year around production of relatively large, long lasting, dark pink flowers which grow in clusters on strong upright stalks. The blossoms are medium large in size and appear massed above a flatly spreading bed of dark green leaves.

BACKGROUND OF THE INVENTION

This new variety of African violet plant originated as a seedling developed by me in my greenhouses at Isernhagen, Germany, where I have been carrying on the breeding and culture of African violets with the object of producing improved varieties for the commercial potted plant market. This new plant was observed to have a very profuse production of dark pink flowers having an attractive wavy characteristic in the petal margins. For these reasons and because the plant appeared to have a vigorous growth habit, it was selected for test and asexual propagation, by leaf cuttings, under my direction at Isernhagen, Germany, has demonstrated that the said characteristics are fixed and hold true from generation to generation. Commercial propagation of this new variety of African violet plant is now being done at West Chicago, Ill., U.S.A., by means of leaf cuttings and division of shoots with no noticeable deviation from the distinctive characteristics of the original plant.

DESCRIPTION OF THE DRAWING

My new variety of African violet plant is illustrated by the accompanying drawing which shows the form and color characteristics of the plant and its blossoms, the color rendition being as nearly true as is reasonably possible to obtain by conventional photographic procedures. The upper view shows details of the blossoms and their supporting stalk and the lower view shows the entire plant and the manner in which the massed blossoms are displaced.

DESCRIPTION OF THE NEW PLANT

The following is a detailed description of my new variety of African violet plant with color identification according to the Horticultural Colour Chart published by the British Colour Council in collaboration with the Royal Horticultural Society.

*The plant*

Origin: Seedling
Parentage:
- *Seed parent.*—An unnamed double pink (unpatented)
- *Pollen parent.*—An unnamed single pink (unpatented)

Classification:
- *Botanic.*—*Saintpaulia ionantha*
- *Commercial.*—African violet Form: Compact potted plant (rosette arrangement)
Height: 3¾ inches from base to top of flowers
Growth: Vigorous and condensed, with fairly strong leaf stems, which are inclined to spread horizontally, and sturdy upright flower stalks Foliage: Quantity—abundant
- *Size of leaf.*—2 to 2½ inches long by 2 to 2½ inches wide
- *Shape of leaf.*—Oblong-ovate with crenate margins
- *Texture.*—Leathery-tough and very tomentose
- *Veins.*—Pinnate—very pronounced on under side of leaf
- *Color.*—Upper side—Parsley Green 00962. Under side—Magnolia Purple 030/1
- *Petioles.*—1¼ to 2 inches long on older leaves

*The bud*

Form: Spherically globular becoming urn-shaped as it opens
Size: Small—¼ inch in diameter and 3/16 inch in depth
Opening: Very slowly—5 weeks from visible bud to opening flower
Color: When petals unfurl—Persian Rose 628/2
Sepals: Hooded over bud for very short period
- *Form.*—5-branched, upstanding and spear-shaped
- *Color.*—Inside—Parsley Green 00962/3. Outside—Maroon 1030 to Parsley Green 00962/2 at tip Calyx:
- *Shape.*—Funnel-shaped, splits to star shape
- *Aspect.*—Smooth on inside, hairy on outside Peduncle: Erect, with a slight crook at basal end, and very tomentose
- *Length.*—⅜ to ½ inch
- *Color.*—Maroon 1030

*The flower*

Blooming character: Recurrent and profuse the year around with production of 40 flowers on 25 to 30 week-old plant
Size of flower: Medium large—15/16 to 1 5/16 inches in diameter. Depth varies with age. Flower is generally flat when fully opened but smaller petals tend to stand up.
Borne: A cluster on each primary peduncle
Shape: Wide and flat cup-shaped when flower first opens, becoming flatter and fuller as bloom develops
Petalage:
- *Number.*—5, three noticeably larger than remaining two
- *Arrangement.*—Sympetalous (fused)
- *Form.*—Rotate, with bilateral symmetry and undulating (wavy) margins
- *Color.*—Top side—Mallow Purple 630/1. Reverse side—Magenta 27/3
- *Texture.*—Soft and flexible
- *Appearance.*—Shiny, almost glittery on upper side, tomentose and velvety on under side Peduncle: 1 1/16 to 1 5/16 inches long before branching then ⅜ to ½ inch long to flower
- *Strength.*—Sturdy and upright
- *Color.*—Maroon 1030

Discoloration after full bloom: Color tends to fade
Effect of weather: Hot weather suppresses flowering and fades the color. Plant and blossoms thrive in 80 to 90% relative humidity.
Fragrance: None
Lasting quality: 10 to 14 days for fully opened flower
Persistence: Blossoms hang on and dry on the stalk

*Reproductive organs*

Stamens:
- *Anthers.*—Dorsifixed, 2 in number, each 1/16 inch long and composed of 2 anther cells
- *Filaments.*—Single filament 3/16 inch long. Color: Persian Rose 628/2
- *Pollen.*—Color—white Pistils: One in number, ⅜ inch in length Stigmas: Color—Persian Rose 628/2
Styles: Color—Persian Rose 628/1, length 3/16 inch
Ovaries: Tomentose and superior The principal features of this new variety of African violet plant are its vigorous growth and its recurrent and profuse production of deep pink flowers the year around. Another feature, of commercial importance to propagators, is the high rate of production of plantlets from each rooted leaf cutting which renders this pink variety of African violet plant a material advance in the art of horticulture.

I claim:

1. A new variety of African violet plant, substantially as herein shown and described, characterized by the unique coloring of its blooms, the profuse and year around blooming habit, and the high rate of production of plantlets from each rooted leaf cutting.

No references cited.

ROBERT E. BAGWILL, Primary Examiner